(12) United States Patent
Stone et al.

(10) Patent No.: US 10,631,843 B2
(45) Date of Patent: Apr. 28, 2020

(54) ANCHOR ASSEMBLY AND METHOD OF USE

(71) Applicant: Biomet Manufacturing, LLC, Warsaw, IN (US)

(72) Inventors: Kevin T. Stone, Winona Lake, IN (US); Gregory J. Denham, Warsaw, IN (US); Ryan A. Kaiser, Leesburg, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 102 days.

(21) Appl. No.: 14/499,930

(22) Filed: Sep. 29, 2014

(65) Prior Publication Data

US 2015/0018880 A1 Jan. 15, 2015

Related U.S. Application Data

(62) Division of application No. 11/744,002, filed on May 3, 2007, now Pat. No. 8,845,685.

(51) Int. Cl.
*A61B 17/04* (2006.01)

(52) U.S. Cl.
CPC ...... *A61B 17/0401* (2013.01); *A61B 17/0469* (2013.01); *A61B 2017/0409* (2013.01)

(58) Field of Classification Search
CPC ............ A61B 17/0401; A61B 17/0469; A61B 2017/0409; A61B 2017/0445; A61B 2017/0446; A61B 2017/0447; A61B 2017/0456; A61B 17/0485; A61F 2002/0888; A61F 2002/0882
See application file for complete search history.

(56) References Cited

U.S. PATENT DOCUMENTS

| | | | |
|---|---|---|---|
| 5,021,059 A | 6/1991 | Kensey et al. | |
| 5,258,016 A | 11/1993 | DiPoto et al. | |
| 5,380,334 A | 1/1995 | Torrie et al. | |
| 5,405,359 A | 4/1995 | Pierce | |
| 5,645,547 A | 7/1997 | Coleman | |
| 5,683,401 A | 11/1997 | Schmieding et al. | |
| 5,702,398 A | 12/1997 | Tarabishy | |
| 5,718,706 A | 2/1998 | Roger | |
| 5,782,864 A * | 7/1998 | Lizardi ............... | A61B 17/0401 606/215 |
| 5,797,928 A | 8/1998 | Kogasaka | |
| 5,827,291 A | 10/1998 | Fucci et al. | |
| 5,902,321 A | 5/1999 | Caspari et al. | |

(Continued)

FOREIGN PATENT DOCUMENTS

WO WO-01/97677 12/2001

OTHER PUBLICATIONS

"U.S. Appl. No. 11/744,002, 312 Amendment filed Aug. 5, 2014", 3 pgs.

(Continued)

*Primary Examiner* — Alexander J Orkin
(74) *Attorney, Agent, or Firm* — Schwegman Lundberg & Woessner, P.A.

(57) ABSTRACT

The present teachings provide a flexible member securing assembly. The flexible member securing assembly includes a shaft, an arm extendable from the shaft, an anchor, and a flexible member grasper formed on a distal end of the arm. Methods of securing a flexible member are also provided.

17 Claims, 10 Drawing Sheets

(56) References Cited

U.S. PATENT DOCUMENTS

| | | | |
|---|---|---|---|
| 5,906,632 A | 5/1999 | Bolton | |
| 5,931,844 A | 8/1999 | Thompson et al. | |
| 5,935,129 A | 8/1999 | McDevitt et al. | |
| 5,980,558 A | 11/1999 | Wiley | |
| 6,099,538 A | 8/2000 | Moses et al. | |
| 6,143,017 A | 11/2000 | Thal | |
| 6,159,235 A | 12/2000 | Kim | |
| 6,174,324 B1 | 1/2001 | Egan et al. | |
| 6,193,754 B1* | 2/2001 | Seedhom | A61F 2/08 623/13.11 |
| 6,355,053 B1 | 3/2002 | Li | |
| 6,368,353 B1 | 4/2002 | Arcand | |
| 6,520,980 B1 | 2/2003 | Foerster | |
| 6,524,317 B1 | 2/2003 | Ritchart et al. | |
| 6,527,795 B1 | 3/2003 | Lizardi | |
| 6,544,281 B2 | 4/2003 | ElAttrache et al. | |
| 6,547,800 B2 | 4/2003 | Foerster et al. | |
| 6,585,730 B1 | 7/2003 | Foerster | |
| 6,641,597 B2* | 11/2003 | Burkhart | A61B 17/0401 606/148 |
| 6,660,023 B2* | 12/2003 | McDevitt | A61B 17/0401 606/232 |
| 6,770,076 B2 | 8/2004 | Foerster | |
| 6,780,198 B1 | 8/2004 | Gregoire et al. | |
| 6,818,010 B2 | 11/2004 | Eichhorn et al. | |
| 6,887,259 B2 | 5/2005 | Lizardi | |
| 7,081,126 B2 | 7/2006 | McDevitt et al. | |
| 7,118,581 B2 | 10/2006 | Friden et al. | |
| 7,144,415 B2 | 12/2006 | Del Rio et al. | |
| 7,749,250 B2* | 7/2010 | Stone | A61B 17/0401 606/232 |
| 7,828,820 B2* | 11/2010 | Stone | A61B 17/0401 606/232 |
| 8,845,685 B2 | 9/2014 | Stone et al. | |
| 2003/0023268 A1* | 1/2003 | Lizardi | A61B 17/0401 606/232 |
| 2003/0109891 A1* | 6/2003 | Dana | A61B 17/0057 606/148 |
| 2003/0195563 A1 | 10/2003 | Foerster | |
| 2003/0204191 A1 | 10/2003 | Sater et al. | |
| 2004/0059341 A1 | 3/2004 | Gellman et al. | |
| 2004/0093031 A1 | 5/2004 | Burkhart et al. | |
| 2004/0097975 A1* | 5/2004 | Rose | A61B 17/0401 606/145 |
| 2005/0107828 A1* | 5/2005 | Reese | A61B 17/0401 606/232 |
| 2005/0283156 A1* | 12/2005 | Schmieding | A61B 17/0401 606/916 |
| 2006/0079904 A1* | 4/2006 | Thal | A61B 17/0401 606/232 |
| 2006/0161183 A1* | 7/2006 | Sauer | A61B 17/0467 606/148 |
| 2006/0178702 A1 | 8/2006 | Pierce et al. | |
| 2006/0235413 A1* | 10/2006 | Denham | A61B 17/0401 606/232 |
| 2006/0259076 A1* | 11/2006 | Burkhart | A61B 17/0401 606/228 |
| 2006/0276841 A1 | 12/2006 | Barbieri et al. | |
| 2006/0293709 A1* | 12/2006 | Bojarski | A61B 17/0401 606/232 |
| 2007/0027477 A1 | 2/2007 | Chudik | |
| 2007/0135843 A1 | 6/2007 | Burkhart | |

OTHER PUBLICATIONS

"U.S. Appl. No. 11/744,002, Examiner Interview Summary dated Jan. 19, 2010", 3 pgs.

"U.S. Appl. No. 11/744,002, Examiner Interview Summary dated Aug. 5, 2010", 3 pgs.

"U.S. Appl. No. 11/744,002, Final Office Action dated Jun. 8, 2010", 13 pgs.

"U.S. Appl. No. 11/744,002, Non Final Office Action dated Dec. 1, 2009", 10 pgs.

"U.S. Appl. No. 11/744,002, Notice of Allowance dated May 23, 2015", 11 pgs.

"U.S. Appl. No. 11/744,002, Preliminary Amendment filed Oct. 13, 2009", 15 pgs.

"U.S. Appl. No. 11/744,002, PTO Response to Rule 312 Communication dated Aug. 15, 2014", 2 pgs.

"U.S. Appl. No. 11/744,002, Response filed Mar. 1, 2010 to Non Final Office Action dated Dec. 1, 2009", 16 pgs.

"U.S. Appl. No. 11/744,002, Response filed Aug. 10, 2010 to Final Office Action dated Jun. 8, 2010", 24 pgs.

"U.S. Appl. No. 11/744,002, Response filed Aug. 21, 2009 to Restriction Requirement dated Jul. 22, 2009", 1 pg.

"U.S. Appl. No. 11/744,002, Restriction Requirement dated Jul. 22, 2009", 9 pgs.

* cited by examiner

ANCHOR ASSEMBLY AND METHOD OF USE

CROSS-REFERENCE TO RELATED APPLICATIONS

This application is a divisional of U.S. patent application Ser. No. 11/744,002 filed on May 3, 2007. The disclosure of this application is incorporated by reference herein in its entirety.

FIELD

The present disclosure relates to apparatus and methods for securing a flexible member using an anchor assembly.

BACKGROUND

The statements in this section merely provide background information related to the present disclosure and may not constitute prior art.

Surgical procedures are often performed on a body, for example, a human body or anatomy, to repair or replace various portions thereof. For example, the soft tissues of the body may need to be reattached to bones due to trauma, overuse, surgical intervention, disease, or other reasons.

Soft tissues can be reattached to bone using fastening devices such as screws, staples, and various types of suture anchors. Soft tissues are often fixed to various positions on the bone. For example, to replace a natural rotator cuff fixation point or to replace the rotator cuff itself, fixing a graft to a selected bone area may be desired. One means to fix a soft tissue to the selected area is to provide a suture through a selected portion of the soft tissue and fix the other end of the suture to a selected area on the bone with the fastener. The use of fasteners in surgical procedures, however, can be improved upon. Accordingly, there is a need for apparatus and surgical methods to facilitate easy and efficient securing of the suture.

SUMMARY

The present teachings provide flexible member securing assemblies to secure the flexible member relative to tissue. The flexible member securing assemblies include a shaft extending along a longitudinal axis from a first end to a second end; an arm extending from the shaft second end; an anchor removably positioned at the shaft second end; and a flexible member grasper formed on a distal end of the arm to position the flexible member in relation to the anchor, wherein the anchor is operable to retain the flexible member in the tissue.

In still other embodiments, the present teachings provide flexible member securing assemblies to secure the flexible member relative to tissue. The flexible member securing assemblies include a shaft extending along a longitudinal axis from a first end to a second end and defining a longitudinal opening therein; an arm positioned in the longitudinal opening and axially extendable from the shaft second end; an anchor removably positioned at the shaft second end and defining a passage to receive the arm; and a flexible member grasper extending from a distal end of the arm to position the flexible member in relation to the anchor; wherein the anchor is operable to retain the flexible member in the tissue.

In various embodiments, methods of securing a flexible member relative to tissue are provided. A hole is formed in the tissue. An anchor is then positioned on a shaft. A flexible member is carried adjacent to a distal end of the anchor and remote therefrom by a removable ledge. The flexible member and anchor are then delivered to the hole in the tissue. The flexible member is secured in the tissue by placing the anchor over the flexible member within the hole in the tissue.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. While rotator cuff repair is disclosed, it is understood that the devices and surgical techniques can easily be adapted for other orthopedic and non-orthopedic uses. The surgical techniques can include minimally invasive and open surgical procedures. The surgical procedures can be used to fix soft tissue, bone, cartilage, and the like. The surgical procedures and devices can be used to fix or join similar tissue types (cartilage to cartilage) or dissimilar tissue types (bone to soft tissue). It is also understood that if the devices and surgical techniques disclosed herein are referred to as being "knotless" or being used without a knot, the knotless feature is directed to the attachment of suture at the anchor portion, however, a knot can also be employed if desired and also be considered "knotless" as used herein.

Referring to FIGS. 1 through 5C, the present teachings provide a flexible member securing assembly 10. The flexible member securing assembly 10 can include a driver 11 comprising a handle 12, a shaft 14, and an arm 16. The flexible member securing assembly 10 also includes an anchor 18 and a flexible member grasper 20.

A flexible member 21 can be made from any biocompatible material that is flexible and can pass through and secure a tissue. Exemplary materials include, but are not limited to, non-resorbable polymers, such as polyethylene or polyester, resorbable polymers, metals, and various combinations thereof. The materials can include those formed into a monofilament, multiple filaments, cables, wires, braids, and the like. In various embodiments, the flexible member 21 can be a hollow material. In various embodiments, the flexible member 21 can be a suture 22.

As further detailed later herein, the flexible member grasper 20 holds a suture 22 in a hole in bone or in other tissue and the suture anchor 18 reinforces the flexible member grasper 20 and holds the suture 22 within the hole in bone or in other tissue. Although various embodiments are detailed in connection with cartilage repairs, such as rotator cuff repair, it is understood that the present teachings can be used in any orthopedic or non-orthopedic application.

Figure 3A:
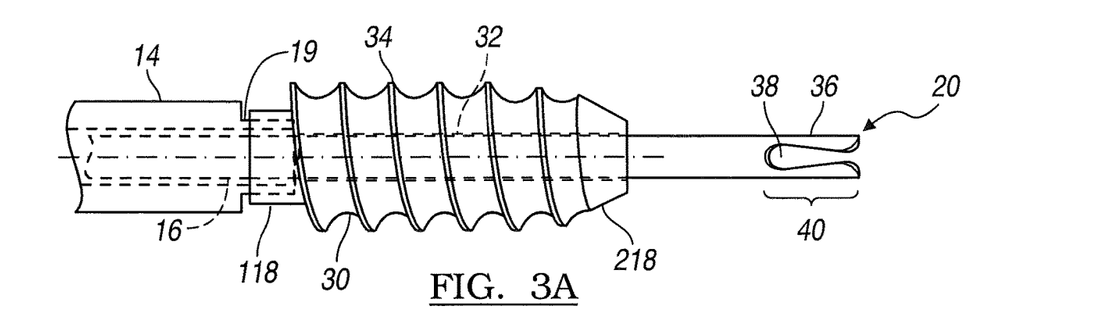
FIGS. 3A and 3B depict variations of a U-shaped flexible member grasper end according to various embodiments.
Figure 3B:
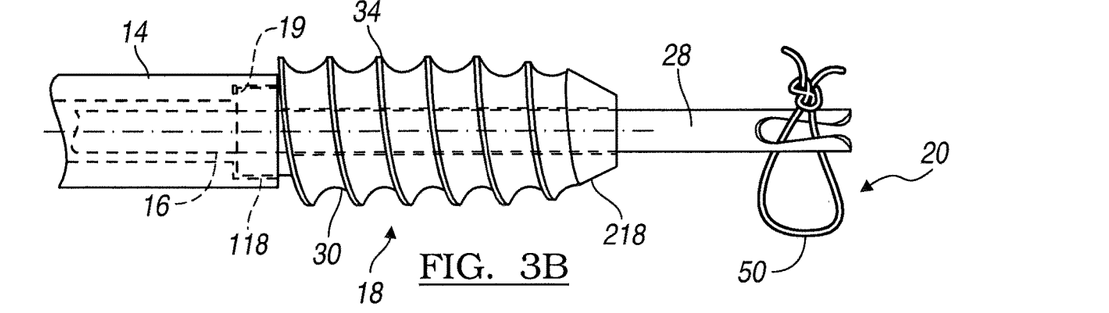
Figure 4A:
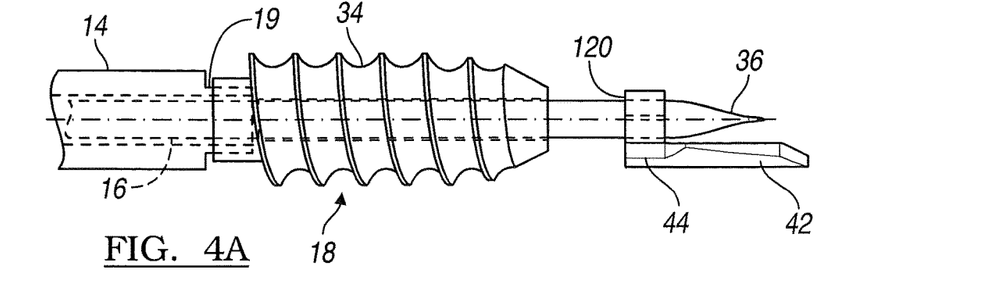
FIGS. 4A through 4D depict the L-shaped flexible member grasper according to various embodiments.
Figure 4B:
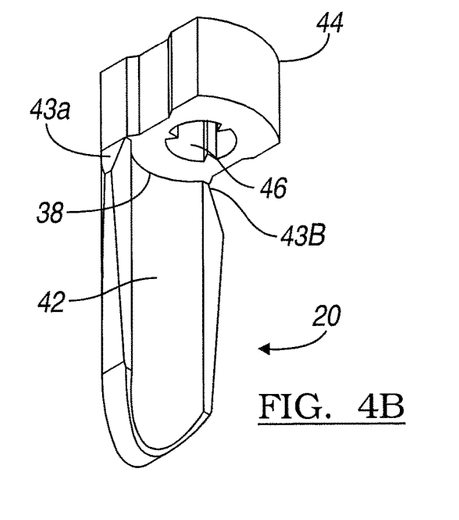
Figure 4C:
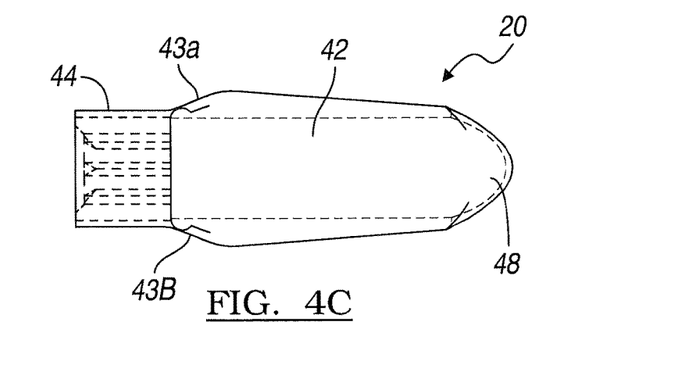
Figure 4D:
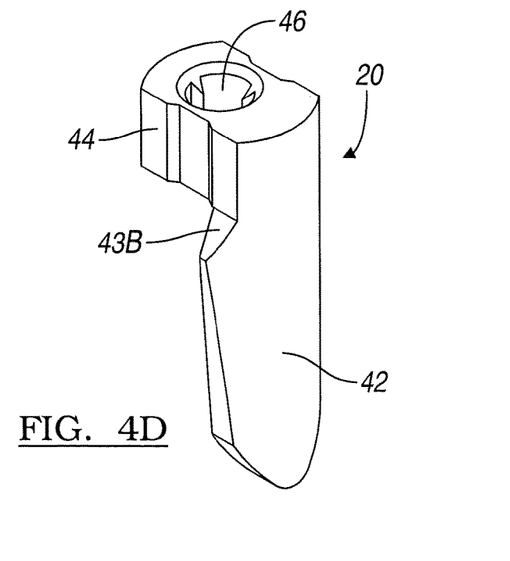

In various embodiments, at the first or proximal end 110 of the flexible member securing assembly 10, there is the handle 12. The handle 12 includes a proximal end 112 and a distal end 212. The handle 12 defines a bore therein to receive the shaft 14 at the handle distal end 212 such that the shaft 14 is in communication with the handle 12. The shaft 14 includes a proximal end 114 and a distal end 214. The arm 16 is contained within at least a region of the shaft 14 and a distal portion of the arm 16 can be extended beyond the shaft distal end 214 upon deployment. The suture anchor 18 is located on a shoulder 19 located at the shaft second or distal end 214, as shown in FIGS. 3A-4A. The shoulder 19 is keyed to axially receive the suture anchor 18 and enable the application of rotational or torsional force. The shoulder 19 can receive the anchor 18 to provide an internal or external mating. The flexible member grasper 20 is located at a first or distal end 216 of the arm 16 which coincides with a second or distal end 210 of the flexible member securing assembly 10. The flexible member grasper 20 is located distal to the suture anchor 18. In various embodiments, the shaft 14, the arm 16, and the suture anchor 18 are concentric and share a common central axis.

Figure 1:
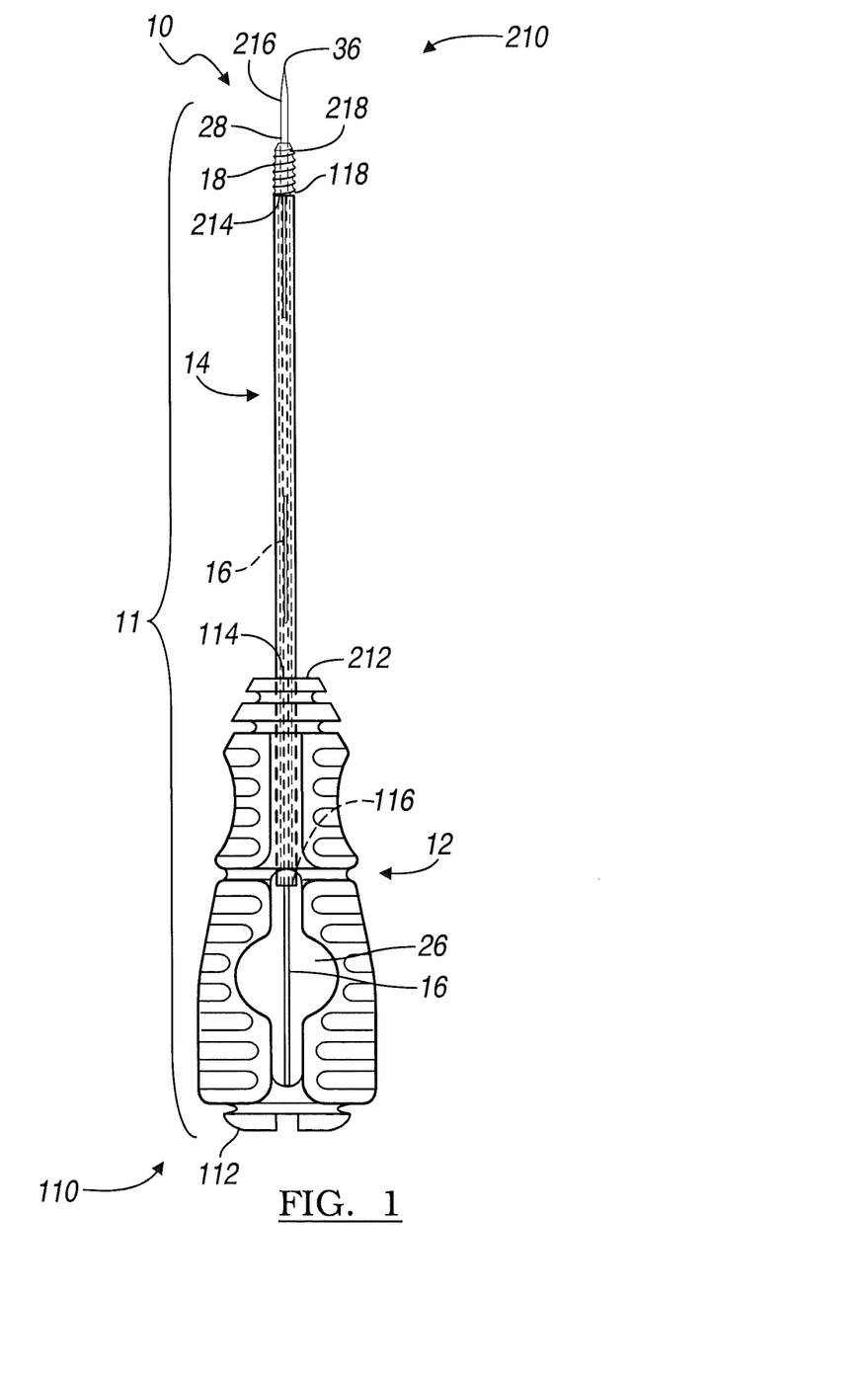
FIG. 1 depicts a flexible member securing assembly according to various embodiments.
Figure 2A:
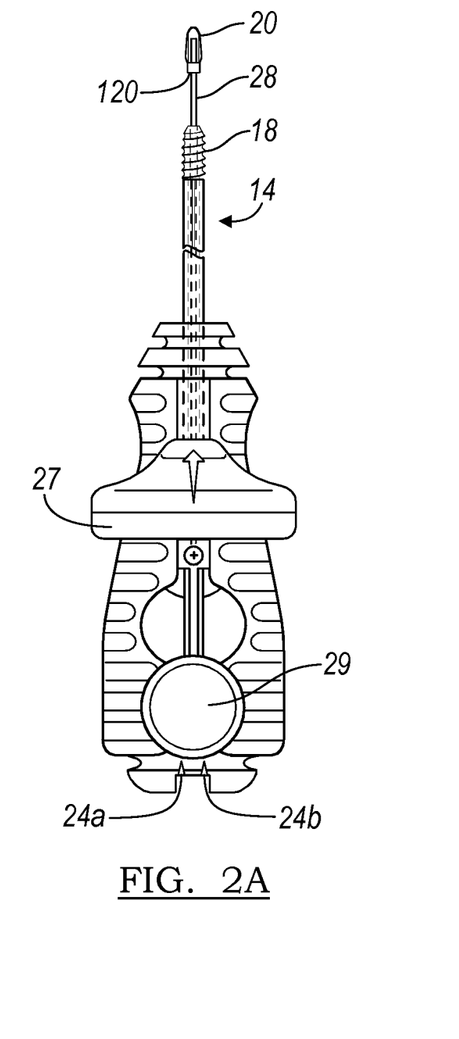
FIGS. 2A and 2B depict various positions of the driver according to various embodiments.

The handle 12 is used to grasp and manipulate the flexible member securing assembly 10. The handle proximal end 112 can include suture channels 24A and 24B in which to direct the suture 22, as shown in FIG. 2A. It is understood that the channels 24A and 24B can be of any appropriate size to hold the suture 22 on the handle 12 without unintentionally dislodging the suture 22. A central portion of the handle 12 defines an opening 26 through which a region of the arm 16 can be housed. In various embodiments, the opening 26 and central portion of the handle 12 include an actuator 27 therein. The actuator 27 can be used to engage the arm 16, such as by axially advancing or retracting the arm 16. When the actuator 27 is depressed, the arm 16 can be advanced or retracted by movement of the actuator 27. The actuator 27 can include a locking feature 29 to control advancement or retraction of the arm 16. The locking feature 29 blocks the actuator 27 from retracting too far.

The handle distal end 212 provides the attachment of and the connection between the handle 12 and the first or proximal end 114 of the shaft 14. The shaft 14 extends longitudinally from the handle 12. In various embodiments, the shaft 14 is molded into the handle 12. The shaft 14 communicates with the handle 12 such that engaging the actuator 27 deploys arm 16 through the shaft 14.

The shaft 14 houses the arm 16 and is sized to allow movement of the arm 16 therefrom. In various embodiments, the shaft 14 includes a longitudinal opening therein. The shaft 14 can be hollow and the arm 16 passes through the hollow opening. In various other embodiments, the shaft 14 can include a groove defined by the surface of the shaft 14 to accommodate the arm 16. The shaft 14 remains stationary during actuation of the flexible member securing assembly 10 as movement of the arm 16 and the actuator 27 are independent from the shaft 14.

Figure 2B:
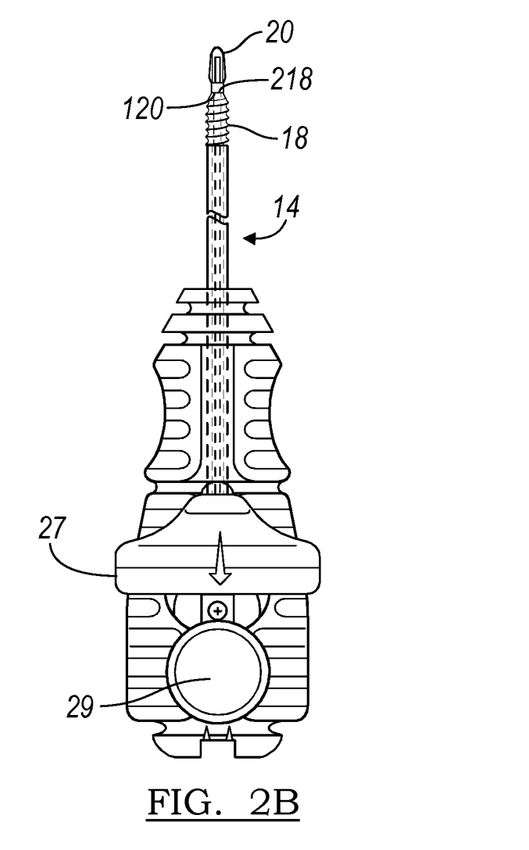
Figure 2C:
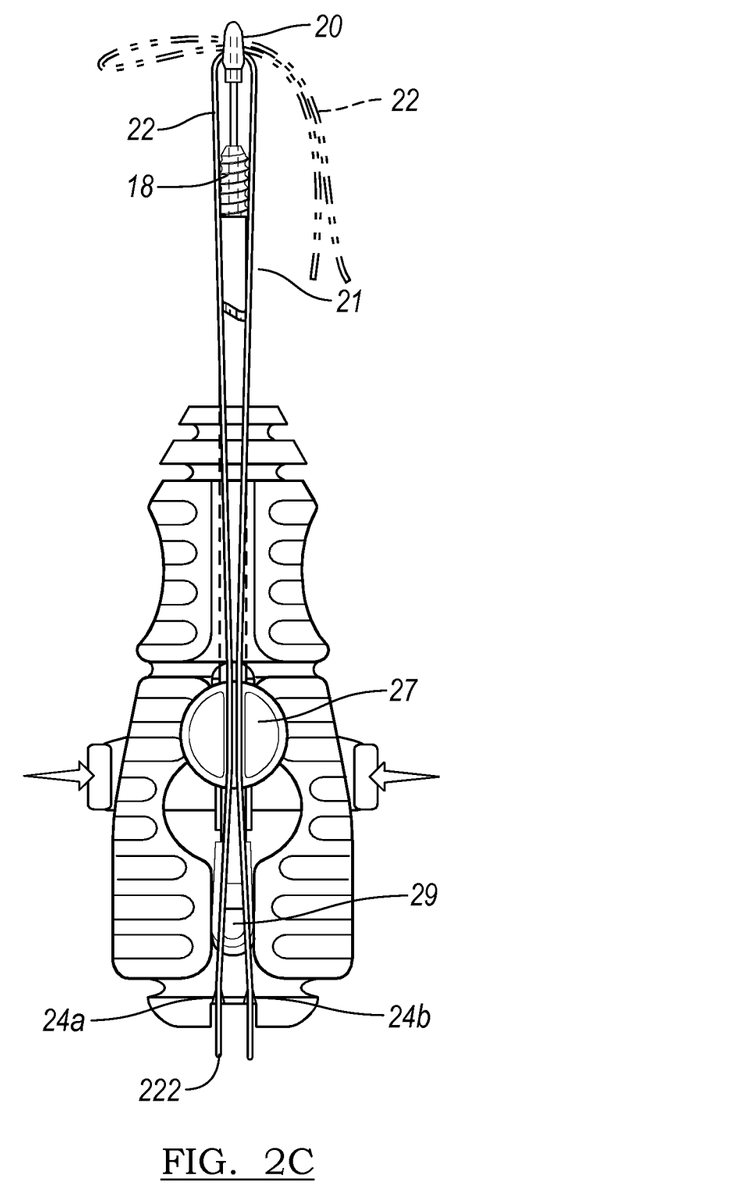
FIG. 2C depicts a close up of the handle of the driver with a suture according to various embodiments.

A first or proximal end 116 of the arm 16 is housed within at least a region of the shaft 14 and the distal end 216 of the arm 16 is axially advanced from within the shaft 14 to a point beyond the shaft distal end 214. In various embodiments, the arm 16 is housed within at least a region of the handle 12, is advanced from within the handle 12, and extends through the shaft 14 to a point beyond the shaft distal end 214. The length of the arm 16 determines how far the flexible member grasper 20 can be extended beyond the shaft distal end 214. In various embodiments, the arm 16 is made of a Nitinol wire. It is understood that the arm 16 can be made of any biocompatible material such as other biocompatible metals, such as titanium, cobalt, chromium, stainless steel, and the like, biocompatible polymers, and composites thereof. FIG. 2A depicts the extended arm 16 and FIG. 2B depicts a retracted arm 16.

Figure 5A:
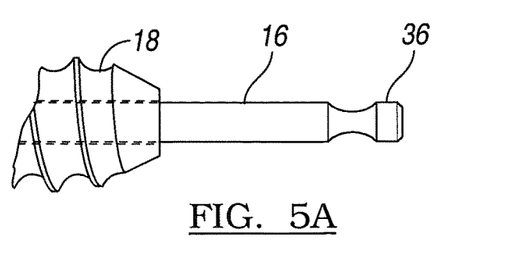
FIGS. 5A through 5C depict various pins according to various embodiments.
Figure 5B:
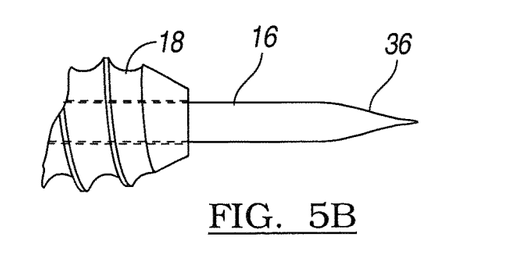
Figure 5C:
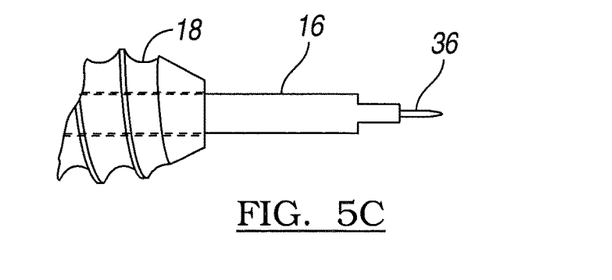

The second or distal end 216 of the arm 16 defines a pin 28. The pin 28 is the region of the arm 16 that extends beyond the shaft distal end 214. The pin 28 is sized to fit through the suture anchor 18 as shown in FIGS. 4A through 5C, and detailed later herein. The pin 28 can also include a tip 36. In various embodiments, the pin tip 36 can form tapered areas such as the point shown in FIG. 4A. The tapered area need not be a continuous taper, but can also include a combination of curved areas and straight areas as shown in FIG. 5A. As shown in FIG. 5C, the tip 36 can include a bulbous or rounded knob used to facilitate grasping the suture 22. The pin 28 can share the same diameter as the rest of the arm 16 or the pin 28 can have varying diameters such as a stepped shoulder or a telescoping diameter to maximize extension of the arm 16 as shown in FIG. 5C. In various embodiments, the pin 28 can define the flexible member grasper 20.

The various pins 28 as shown in FIGS. 4A and 5A through 5C can be substituted or interchanged according to the present teachings. It is understood that the features of one pin can be incorporated into other embodiments and such combinations are within the scope of the present teachings. For example, as shown in FIGS. 3A and 3B, the pin 28 includes a U-shaped region having a closed loop of suture 50 thereon and defining the flexible member grasper 20.

Referring to FIGS. 1 through 5C, the anchor 18 includes an anchor body 30 defining a bore 32. The anchor 18 can be a suture anchor, a bone screw, or other fixation device. The bore 32 extends through the anchor body 30 and is used to place the suture anchor 18 on the shaft distal end 214, via a first or proximal end 118 of the anchor 18. The bore 32 provides passage of the arm 16 and the pin 28 beyond the shaft distal end 214. The bore 32 can be slidably received on the mating keyed shoulder 19 on the shaft 14 and can be sized to provide a snug fit and removable fixation of the anchor 18 to the shaft 14. The shoulder 19 can have the same cross-section shape as the shaft distal end 214 or have a different cross-section shape, such as a rounded shaft 14 being mated to a squared shoulder 19. As shown in FIGS. 3A and 3B, the shaft distal end 214 can fit inside of the suture anchor proximal end 118 or on the outside of the suture anchor proximal end 118, respectively. It is understood that any combination of shoulder 19 and shaft 14 sizes and shapes can be used with the present teachings.

The snug fit prevents movement of the anchor 18 when the arm 16 and pin 28 are advanced through the bore 32 and out of the anchor 18 or retracted along the same path. The bore 32 can be sized to provide an interference fit between the bore 32 and a proximal end 120 of the flexible member grasper 20.

The anchor 18 can include tissue engaging or bone engaging surface features 34 to fix the anchor 18 in the hole in tissue or bone. As depicted, the bone engaging surface features 34 are threads. It is understood that any suitable bone engaging surface feature can be used to fix the anchor 18 in the bone. In embodiments where the suture 22 is secured by trapping the suture 22 between a wall of the hole in bone and an outer perimeter or surface of the anchor 18, it is understood that the anchor 18 can be free from sharp points or edges that might damage or cut the suture 22.

The anchor 18 can be formed of any appropriate material. As non-limiting examples, the anchor 18 can be formed of various biocompatible polymers and co-polymers, such as polyetheretherketone (PEEK), polymers or co-polymers of polylactic acid and polyglycolic acid, metals, such as titanium, stainless steel, or alloys of cobalt, chromium, etc., and composites thereof. The anchor 18 can also be formed of a composite material made of any of the above materials.

The flexible member grasper 20 is located at a second or distal end 218 of the anchor 18. In various embodiments, the flexible member grasper 20 is remote from the anchor 18 or is at some length on the arm 16 away from the anchor 18 to accommodate the anchor 18 being passed over the suture 22 without extending the arm 16, as detailed later herein. Referring the FIGS. 3A and 3B, the flexible member grasper 20 is defined by the pin 28 at a pin tip 36. In such embodiments, the pin tip 36 includes a channel 38 therein as formed by the U-shaped region 40. The U-shaped region 40 can be sized to receive a single suture 22 therein or can be sized to receive folded regions of suture 22 therein. It is understood that a full U-shape, a J-shape, or any other shape can be used to hold the suture 22.

Turning to FIG. 3B, in various embodiments, the flexible member grasper 20 can also include a closed suture loop 50 in combination with the pin tip 36 or the channel 38. The closed suture loop 50 is placed at the pin tip 36 or near the distal end of the pin 28. The closed suture loop 50 can be fused onto the pin tip 36 or the distal end of the pin 28. The closed suture loop 50 carries the suture 22. The suture loop 50 can be used to make small eyelet or channel 38 able to accommodate a suture 22 (or folded over suture 22) that may otherwise be too large to fit within the channel 38.

Referring to FIGS. 4A through 5C, the flexible member grasper 20 can be defined by the pin 28, the pin tip 36, and a shoulder 44 having the ledge 42 extending from the shoulder. The shoulder 44 defines a bore 46 to engage the pin tip 36. In various embodiments, the bore 46 can be concentric with the pin 28 and the shaft 14 so that the flexible member grasper 20 is advanced or retracted simultaneously with the arm 16 and motion of the arm 16 is translated to the flexible member grasper 20 through the shaft 14. The bore 46 can removably slide or snap onto the pin tip 36. In various embodiments, a region of the pin tip 36 can be slightly larger than the bore 46 or it can have a tapered internal surface such that the flexible member grasper 20 easily slides onto the pin, but provides resistance as to unintentional removal from the pin 28 (for example, removal prior to insertion of the pin 28 in a hole in bone or into a bone).

The ledge 42 extends away from the shoulder 44 at any angle, such as between 45 and 90 degrees, as non-limiting examples. As shown in FIGS. 4A through 4D, the shoulder 44 and the ledge 42 can abut to form a rough L-shape flexible member grasper 20. The angle of the ledge 42 can be selected to facilitate advancing the flexible member grasper 20 through a cannula in a minimally invasive procedure, for example, or to adequately engage a bone, as detailed later herein. The shoulder 44 and ledge 42 meet to provide the channel 38 for the suture 22. Securing the suture 22 between the shoulder 44 and the ledge 42 is enhanced by the indentations 43A and 43B on the ledge 42. In various other embodiments, securing of the suture 22 on the flexible member grasper 20 is achieved by arranging the suture 22 between the pin tip 36 and the ledge 44 and guiding the suture along the shoulder 44.

The flexible member grasper 20 can be made of a low-friction material and have a generally smooth exterior so the flexible member grasper 20 can easily slide into and out of the hole in bone for temporary placement of the flexible member grasper 20 or can easily slide into and is fixed in the bone for permanent placement of the flexible member grasper 20. The materials for the flexible member grasper 20 can be selected from the materials useful for the suture anchor 18 as detailed above. In various embodiments, the flexible member grasper 20 is made of PEEK. The low friction materials allow the flexible member grasper to easily slide in a hole in bone or be placed and fixed into the bone. In embodiments where the flexible member grasper 20 is adapted to be permanently fixed into the bone, the ledge 42 can include a ledge nose 48 that is slightly angled or tapered to engage the bone without damaging the suture. For example, the ledge nose 48 can include a more angled region by which to help contain the suture 22. As shown in FIGS. 4A through 4D, the ledge 42 has a generally triangular shape having rounded edges or is shovel-like in shape.

Figure 6A:
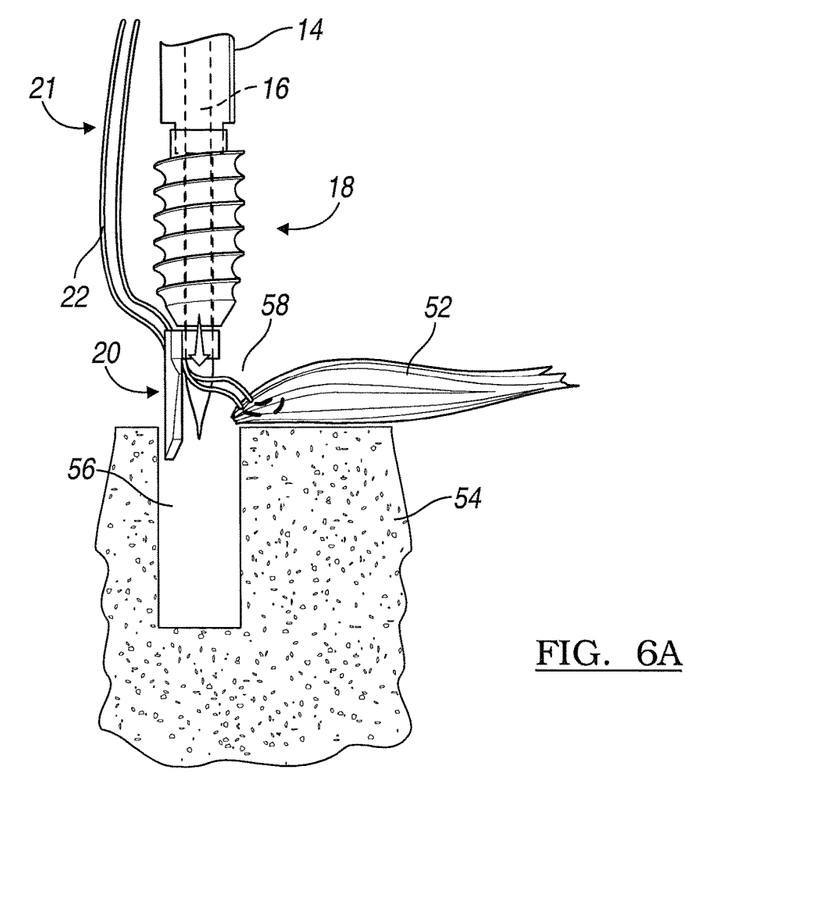
FIGS. 6A through 6C depict a method of using a flexible member securing assembly according to various embodiments.
Figure 6B:
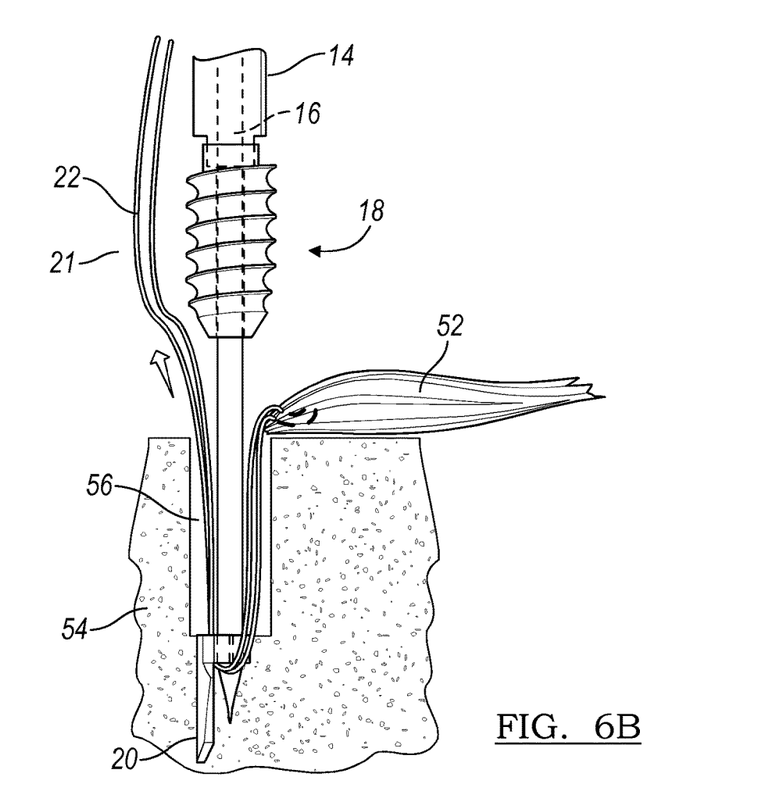
Figure 6C:
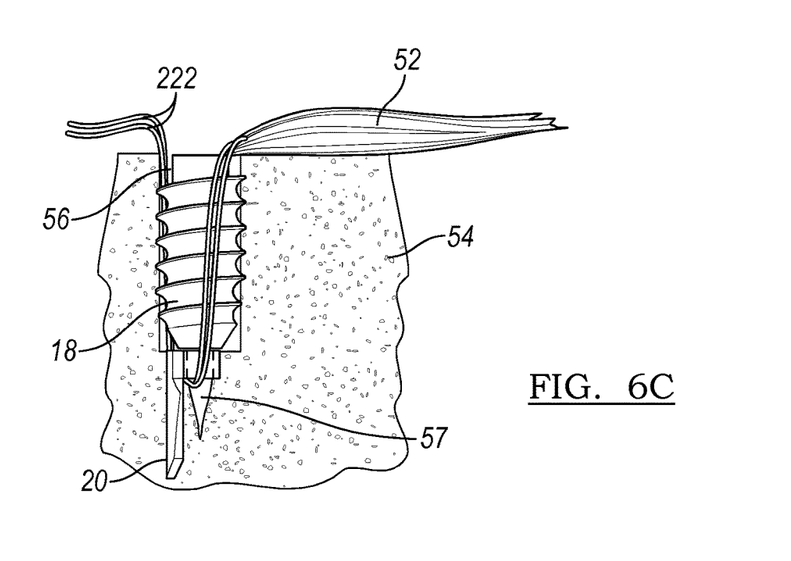

Referring to FIGS. 6A through 6C, the present teachings provide methods of securing a suture 22. The flexible member securing device 10 can be used to fix a soft tissue 52 to a bone 54 via a bone hole 56 at a defect site 58. The bone hole 56 can be pre-formed and is of a depth sufficient to house the anchor 18 and in various embodiments, to also have the flexible member grasper 20 fixed under the anchor 18 within the bone hole 56. The bone hole 56 can have a width to match the anchor 18 or a smaller width to provide an interference fit with the suture anchor.

The suture 22 can be sewn, looped through, or tied to a tissue 52 or connected to another device or graft. The suture 22 is then loaded onto the suture grasper 20 using various embodiments of the flexible member securing assembly 10 detailed above. In use, the suture 22 is arranged about the ledge 42 of the flexible member grasper 20. The flexible member grasper 20 carrying the suture 22 thereon is then placed into the bone hole 56. The suture 22 is reinforced by placing the anchor 18 over the flexible member grasper 20 within the bone hole 56 to trap suture 22 in bone hole 56.

As shown in FIGS. 2C, 4A through 4D, and 5A, the suture 22 can be arranged about the ledge 42 to secure the suture 22 on the flexible member grasper 20. The suture 22 is aligned or guided between the pin 28 or the pin tip 36 and the ledge 42. The suture 22 can rest in the channel 38 and/or against the shoulder 44. The suture 22 then extends along the exterior of the shaft 14. In various embodiments, the shaft 14 can include a region in which the suture 22 can extend therein. The suture 22 can be secured to the suture channels 24A and 24B. As indicated by the phantom line, suture 22 can be placed in any suitable position and need not be secured to the suture channels 24A and 24B.

As shown in FIGS. 3A and 3B, in embodiments where the pin tip 36 defines the flexible member grasper 20, the suture 22 and/or suture loop 50 can be placed on the channel 38 to hold the suture in the grasper. For example, with the U-shaped 40 area, described above, the suture 22 and/or suture loop 50 can be arranged or disposed within the U-shape. Particular to FIG. 3B, the suture 22 can be passed through the closed suture loop 50 contained by the channel 38.

Referring to FIG. 6B, the flexible member grasper 20 is then placed in the bone hole 56 by advancing flexible member securing assembly 10 towards the bone hole 56 and actuating the arm 16. The pin 28 is then extended into the bone hole 56 to place the flexible member grasper 20 in the bone hole 56. In embodiments where the flexible member grasper 20 is remote from the anchor 18 at some distance on the arm 16, the arm 16 need not be actuated to place the flexible member grasper 20 in the bone hole 56.

Placing the flexible member grasper 20 can include temporarily placing the flexible member grasper 20 in the hole in bone to a depth sufficient to allow the anchor 18 to also enter the bone hole 56. In such embodiments, the flexible member grasper 20 is removed upon placement of the anchor 18. In various other embodiments, placing the flexible member grasper 20 includes permanently fixing the flexible member grasper 20 due to the flexible member grasper 20 biting into the bone 54. In such embodiments, the flexible member grasper 20 will remain at the defect site 58 under the anchor 18, as shown in FIG. 6C.

When the flexible member grasper 20 has confined the suture 22 in the bone hole 56, the suture 22 can be tightened to provide the appropriate tension at the defect site 58 or to tighten the suture 22 in the adjacent soft tissue 52. The suture 22 can be tightened by engaging the free ends 222 of the suture 22 or sutures. In minimally invasive procedures, the suture 22 can be tightened by pulling on the suture free ends 222 outside of the cannula. In various embodiments, the locking feature 29 on the handle 12 is engaged to prevent any unintentional movement of the flexible member grasper 20 out of the bone hole 56 until the final securing of the suture 22.

After the flexible member grasper 20 has been placed in the bone hole 56 for temporary placement or permanent fixation, the suture 22 is reinforced in the bone hole 56 by placing the anchor 18 over the flexible member grasper 20 within the bone hole 56. The anchor 18 can be pushed, rotated, or tapped into the bone hole 56. The anchor 18 and the shaft distal end 214 are advanced into the bone hole 56 such that the bone engaging surface features 34 on the anchor 18 engage the bone 54 and thereby fix the suture anchor 18 in the bone hole 56.

In embodiments where the pin tip 36 defines the flexible member grasper 20, the flexible member grasper 20 is removed from the defect site 58 by engaging the actuator 27 to retract the arm 16. For example, in embodiments such as those represented by FIG. 3B, the closed suture loop 50 portion carrying the suture 22 is placed in the bone hole 56 for permanent fixation after the pin tip 36 is removed from the defect site 58. The anchor 18 is deposited over the closed suture loop 50 and the arms of the suture 22 extend along the anchor 18 and are trapped between the walls of the bone hole 56 and the anchor 18. The closed suture loop 50 acts like the removable ledge and is placed in the bone hole 56 below the anchor 18.

As shown in FIG. 6C, a hole 57 can remain in the bone 54 as a result of the pin tip 36 engaging the bone 54 and being subsequently removed. If needed, the locking feature 29 is disengaged to allow the arm 16 to be retracted. In embodiments where the flexible member grasper 20 permanently remains in the bone hole, upon engaging the actuator, the arm 16 is removed from the defect site, and the flexible member grasper 20 remains in the bone hole 56 below the anchor 18.

The suture 22 is positioned on the outer surface of the suture anchor 18 thereby trapping the suture 22 between the anchor 18 and the bone hole 56. The suture 22 can be screwed, pushed, or tapped into place. It may be useful to have the shoulder 19 or the shaft distal end 214 include a swivel feature to allow the flexible member grasper 20 to place the suture in the bone hole 56 and allow the anchor 18 to be placed into the bone hole 56 while minimizing tangling of the suture 22 in the bone hole 56. By trapping the suture 22 between the anchor 18 and the bone hole 56, the suture 22 is secured in the bone hole 56 and the tissue can be secured without using a knot.

Figure 7A:
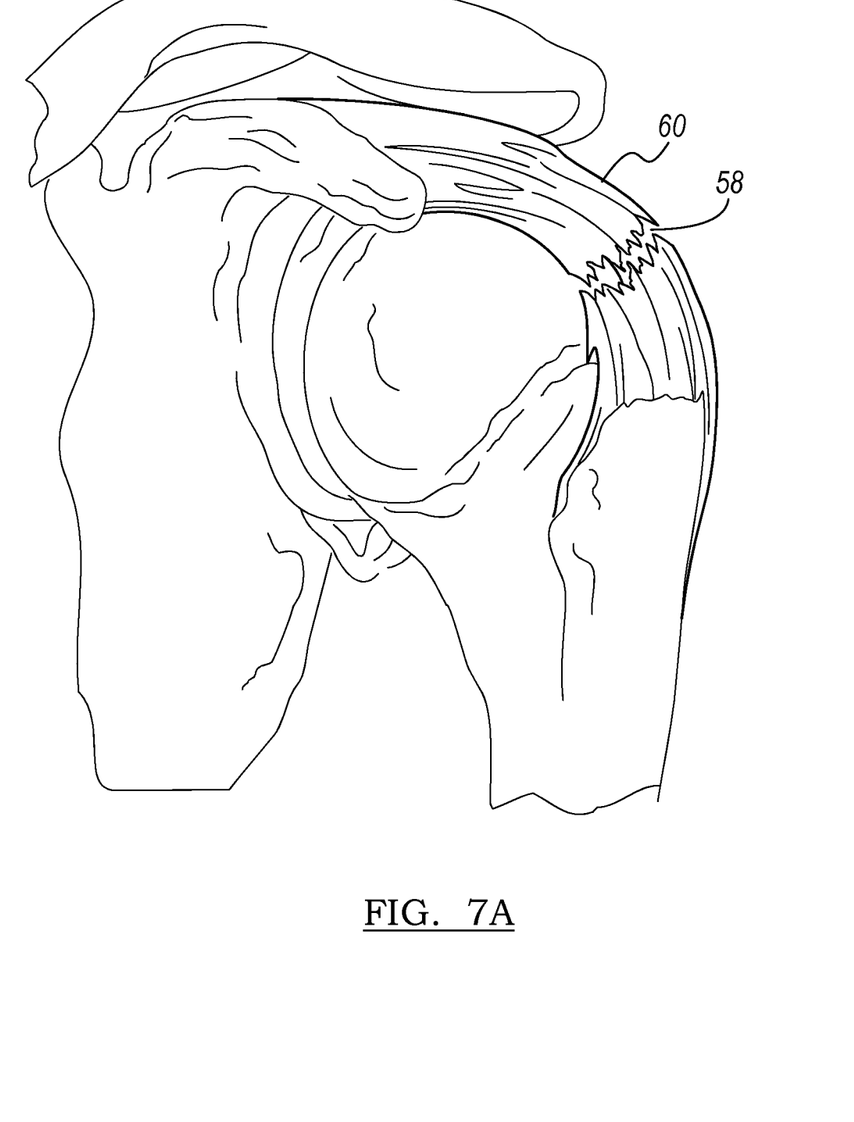
FIGS. 7A through 7C depict a method of securing a rotator cuff according to various embodiments.
Figure 7B:
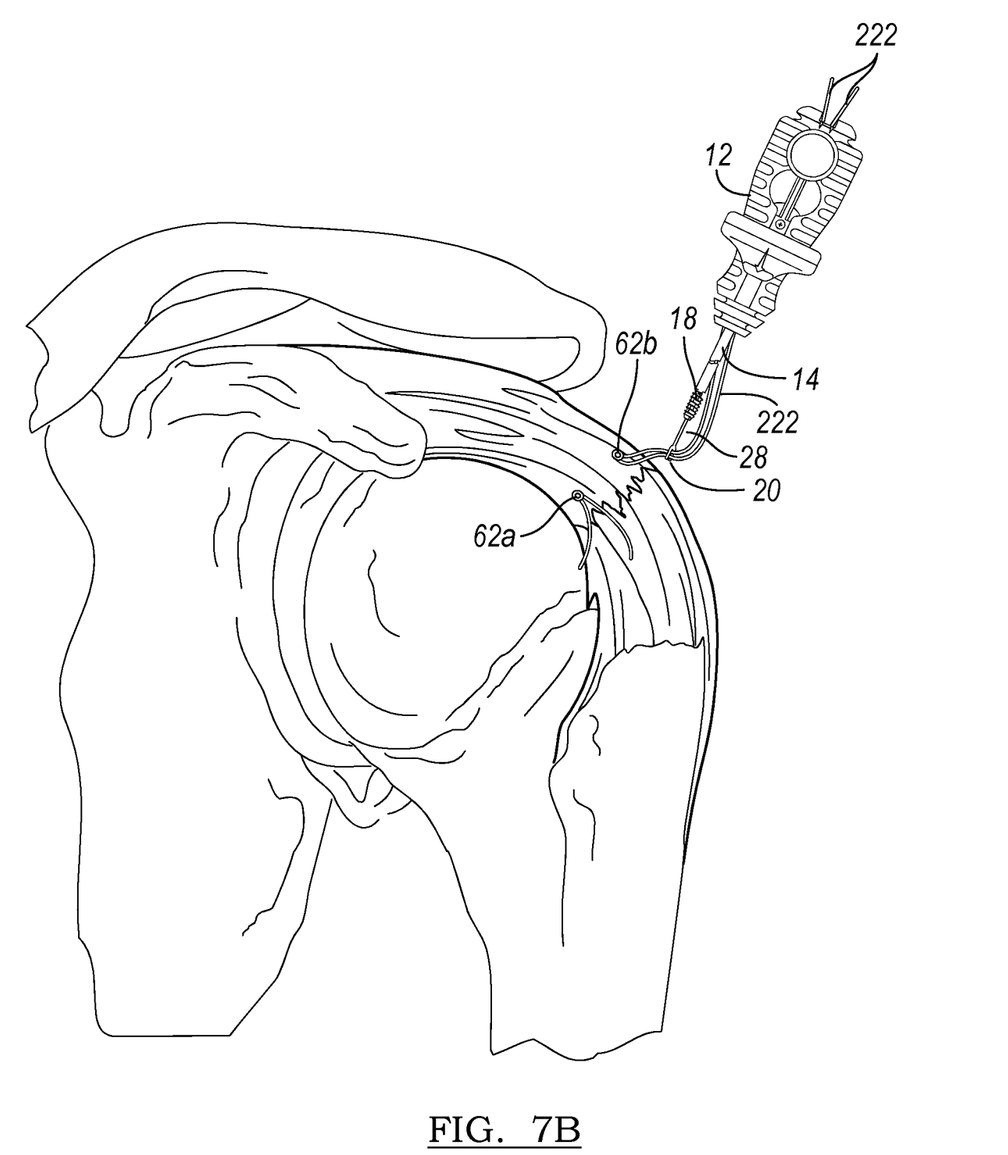
Figure 7C:
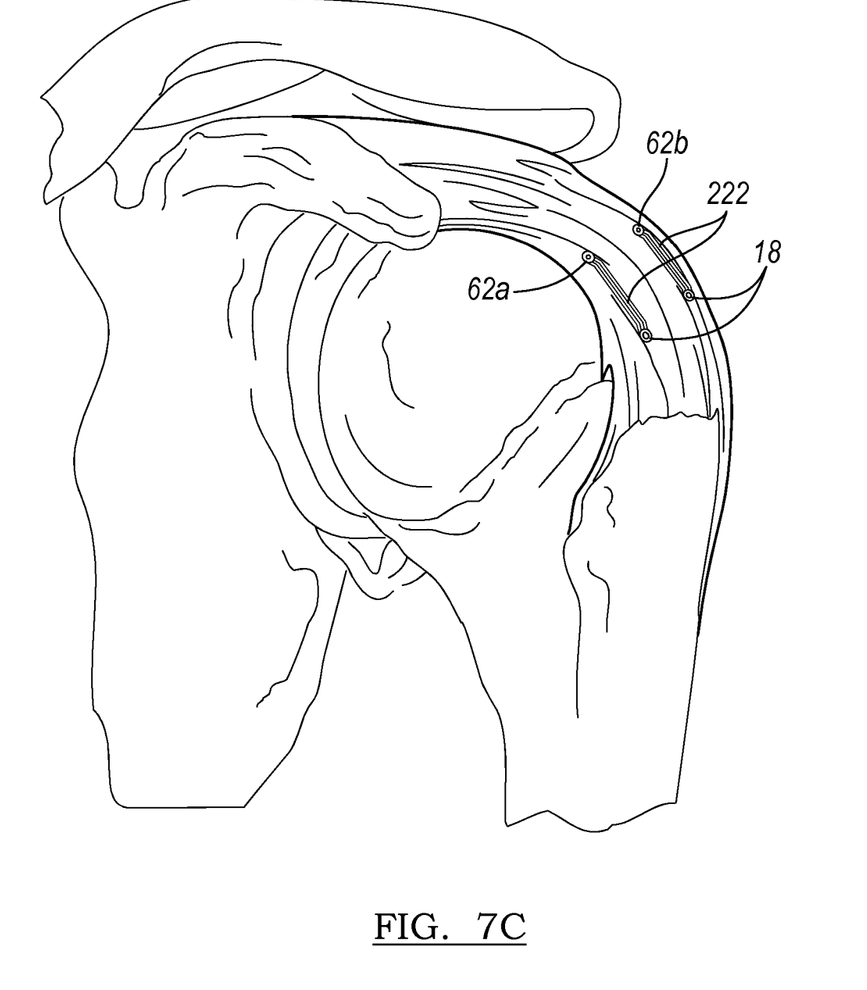

In still other embodiments, the flexible member securing techniques can be used to perform rotator cuff 60 repair as shown in FIGS. 7A through 7C. The rotator cuff 60 (and any grafts, if used) is stretched over the defect site 58 and secured to a first position on a surrounding area of bone using at least one medial row anchor, such as medial row anchors 62a and 62b. The medial row anchors 62a and 62b carry suture 22 having free ends 222. The free ends 222 are available for additional suturing at the rotator cuff 60 defect site 58, if desired.

As shown in FIG. 7B, the flexible member securing assembly 10 depicted in FIG. 3A is used to grasp the free ends 222 of the suture in the medial row anchors 62a and 62b. The free ends 222 are arranged in the U-shaped region 40 of the flexible member grasper 20 as detailed above herein. The flexible member grasper 20 is then placed into a bone hole 56 which is offset from the medial row anchors 62a and 62b. The offset flexible member grasper 20 can be placed lateral to the medial row anchors 62A and 62B in various embodiments. Next, the suture is tensioned to tighten and secure the rotator cuff 60 and to increase the footprint of the repair. The flexible member grasper 20 holds the suture 22 while it is tensioned.

Subsequently, the anchor 18 (or several anchors) is placed over the suture free ends 222 to trap the suture free ends in the bone hole 56. FIG. 7C shows each medial row anchor 62a and 62b being connected to a separate anchor 18 and 18', but is understood that several medial row anchors can be connected with a single anchor 18.

Connecting the medial row anchors 62a and 62b to other anchors located lateral thereto provides a medial and lateral row repair or a double row repair. In various embodiments, the flexible member securing assembly 10 can be used to place two or more additional rows of anchors. As shown in FIG. 6C, the anchors 18 and 18' are secured to the defect site 58 lateral to and parallel with the medial row anchors 62a and 62b. In other embodiments, the anchors 18 can be secured to the defect site 58 in a criss-cross pattern, a grid, free-form, or any other suitable design.

Such repairs maximize the footprint of the rotator cuff 60 and provide enhanced strength to the defect site. Moreover, this technique prevents tying off the suture free ends 222 at the medial row anchors 62a and 62b using knots. Instead, the suture 22 is held at an appropriate tension to secure the rotator cuff 60. The free ends of the suture 222 can be cut upon securing the suture with the anchors 18 and 18'.

The description of the teachings is merely exemplary in nature and, thus, variations that do not depart from the gist of the teachings are intended to be within the scope of the teachings. Such variations are not to be regarded as a departure from the spirit and scope of the teachings.

What is claimed is:

1. A flexible member securing assembly to secure a flexible member relative to tissue comprising:

a shaft extending along a longitudinal axis from a first end to a second end;
an arm extending from the shaft second end;
a closed loop suture;
an anchor removably positioned at the shaft second end; and
a flexible member grasper formed on a distal end of the arm to position the flexible member in relation to the anchor, the flexible member grasper including a U-shaped region open on a distal end of the arm, the U-shaped region defining a channel, the closed loop suture positioned within and fused to the channel of the U-shaped region with the flexible member extending through the closed loop suture, wherein the closed loop suture is sized and configured to accommodate a flexible member that is larger than the channel of the U-shaped region and such that the flexible member is positioned at the distal end of the arm distally from the anchor, and wherein the flexible member is separate from and not integral to the closed loop suture, wherein the flexible member securing assembly has a delivery configuration in which the closed loop suture is separate from and remote from the anchor so that during implantation the closed loop suture and the flexible member extending through the closed loop suture can be positioned at a bottom of a hole in bone before the anchor is implanted in the hole and wherein the anchor is operable to retain the flexible member in the tissue.

2. The flexible member securing assembly of claim 1, wherein the shaft, the arm, and the anchor are concentric along the longitudinal axis.

3. The flexible member securing assembly of claim 1, wherein the flexible member grasper is remote from the anchor.

4. The flexible member receiving assembly of claim 1, wherein the shaft defines an opening to axially move the arm independent of the shaft.

5. The flexible member securing assembly of claim 1, wherein at least a portion of the flexible member grasper is removably fixed to the distal end of the arm.

6. The flexible member securing assembly of claim 1, wherein the flexible member grasper is defined by a region of the distal end of the arm.

7. The flexible member securing assembly of claim 1, wherein the anchor comprises a body defining a through bore, wherein the arm axially extends through the through bore.

8. The flexible member securing assembly of claim 1, wherein the anchor comprises a body defining a bore, wherein the anchor bore is keyed to receive a mated shoulder defined by the shaft second end.

9. The flexible member securing assembly of claim 1, wherein the flexible member is selected from the group consisting of suture, wire, cable, and braided filaments.

10. A flexible member securing assembly to secure a flexible member relative to tissue comprising:
a shaft extending along a longitudinal axis from a first end to a second end and defining a longitudinal opening therein;
an arm positioned in the longitudinal opening and axially extendable from the shaft second end;
a closed loop suture;
an anchor removably positioned at the shaft second end and defining a passage to receive the arm; and
a flexible member grasper extending from a distal end of the arm to position the flexible member in relation to the anchor, the flexible member grasper including a U-shaped region open on a distal end of the arm, the U-shaped region defining a channel, and the closed loop suture positioned within and fused to the channel of the U-shaped region with the flexible member extending through the closed loop suture, wherein the closed loop suture is sized and configured to accommodate a flexible member that is larger than the channel of the U-shaped region and such that the flexible member is positioned at the distal end of the arm distally from the anchor, and wherein the flexible member is separate from and not integral to the closed loop suture, wherein the flexible member securing assembly has a delivery configuration in which the closed loop suture is separate from and remote from the anchor so that during implantation the closed loop suture and the flexible member extending through the closed loop suture can be positioned at a bottom of a hole in bone before the anchor is implanted in the hole, and wherein the anchor is operable to retain the flexible member in the tissue.

11. The flexible member securing assembly of claim 10, wherein the flexible member grasper is remote from the anchor and is removable from the distal end of the arm.

12. The flexible member securing assembly of claim 10, wherein the flexible member grasper is defined at least in part of the distal end of the arm.

13. The flexible member securing assembly of claim 12, wherein the flexible member grasper defines a channel to receive the suture.

14. The flexible member securing assembly of claim 10, further comprising a handle extending from the shaft.

15. The flexile member securing assembly of claim 14, further comprising an actuator on the handle operable to move the arm.

16. A flexible member securing assembly to secure a flexible member relative to tissue comprising:
a handle;
a shaft extending from the handle;
an arm axially extendable relative to the shaft;
a closed loop suture;
a flexible member grasper at a distal end of the arm configured to position the flexible member relative to the tissue; and
an anchor removably positioned at a distal end of the shaft, the flexible member grasper including a U-shaped region open on a distal end of the arm, the U-shaped region defining a channel, and the closed loop suture positioned within and fused to the channel of the U-shaped region with the flexible member extending through the closed loop suture, wherein the closed loop suture is sized and configured to accommodate a flexible member that is larger than the channel of the U-shaped region and such that the flexible member is positioned at the distal end of the arm distally from the anchor, and wherein the flexible member is separate from and not integral to the closed loop suture, wherein the flexible member securing assembly has a delivery configuration in which the closed loop suture is separate from and remote from the anchor so that during implantation the closed loop suture and the flexible member extending through the closed loop suture can be positioned at a bottom of a hole in bone before the anchor is implanted in the hole, and wherein the anchor is configured to retain the flexible member in the tissue.

17. The flexible member securing assembly of claim 16, wherein the flexible member grasper includes a U-shaped channel formed in the distal end of the arm to retain the flexible member.

* * * * *